US010032237B1

(12) United States Patent
Lachs et al.

(10) Patent No.: US 10,032,237 B1
(45) Date of Patent: Jul. 24, 2018

(54) PHYSICIAN PERFORMANCE AND RECOMMENDATION INTERFACE

(71) Applicant: The Advisory Board Company, Washington, DC (US)

(72) Inventors: Marc Lachs, Austin, TX (US); Cheng Zhou, Austin, TX (US); Nathan Thompson, Bethesda, MD (US)

(73) Assignee: THE ADVISORY BOARD COMPANY, Washington, DC (US)

( * ) Notice: Subject to any disclaimer, the term of this patent is extended or adjusted under 35 U.S.C. 154(b) by 852 days.

(21) Appl. No.: 14/309,588

(22) Filed: Jun. 19, 2014

(51) Int. Cl.
*G06F 9/44* (2018.01)
*G06Q 10/00* (2012.01)
*G16H 10/00* (2018.01)
*G06F 7/00* (2006.01)
*G06F 17/00* (2006.01)
*G06Q 50/22* (2018.01)
*G06Q 10/06* (2012.01)

(52) U.S. Cl.
CPC ......... *G06Q 50/22* (2013.01); *G06Q 10/0639* (2013.01)

(58) Field of Classification Search
CPC .. G06Q 10/10; G06Q 50/24; G06Q 10/06393; G06Q 50/22; G06F 19/327
USPC ........................................................ 705/2-3
See application file for complete search history.

(56) References Cited

U.S. PATENT DOCUMENTS

| 8,731,966 | B2 * | 5/2014 | Breitenstein | G06Q 10/10 705/3 |
| 2006/0161456 | A1 * | 7/2006 | Baker | G06F 19/327 705/2 |
| 2008/0133290 | A1 * | 6/2008 | Siegrist | G06Q 10/00 705/2 |
| 2008/0288286 | A1 * | 11/2008 | Noreen | G06Q 10/06 705/2 |
| 2013/0117033 | A1 * | 5/2013 | Mohlenbrock | G06Q 50/22 705/2 |

* cited by examiner

*Primary Examiner* — Joy Chng
(74) *Attorney, Agent, or Firm* — Bookoff McAndrews, PLLC

(57) ABSTRACT

The technology provides for utilizing and displaying physician analytics. For example, a result metric for a physician is based on a value metric, a quality metric, and/or a quantity metric. The value metric, quality metric, and/or quantity metric may all be received from different sources. The result metric may be displayed on a chart, or the result metric may be utilized for determining referral recommendations for a physician. The result metric may be displayed as a physician indicator on the chart. An insight for the physician may also be determined from the result metric. The insight may be based on the location of the physician indicator on the chart, and the insight may be represented by the color or other visual attribute of the physician indicator. For referral recommendations, the result metric may be used to adjust the rank of a physician in a referral search result.

20 Claims, 13 Drawing Sheets

| Insight | Value Metric | Quality Metric | Quantity Metric |
|---|---|---|---|
| Insight No. 1 | Less Than Average | Higher Than Average | Higher Than Average |
| Insight No. 2 | Less Than Average | Higher Than Average | Less Than Average |
| Insight No. 3 | Less Than Average | Less Than Average | Higher Than Average |
| Insight No. 4 | Less Than Average | Less Than Average | Less Than Average |
| Insight No. 5 | Higher Than Average | Higher Than Average | Higher Than Average |
| Insight No. 6 | Higher Than Average | Higher Than Average | Less Than Average |
| Insight No. 7 | Higher Than Average | Less Than Average | Higher Than Average |
| Insight No. 8 | Higher Than Average | Less Than Average | Less Than Average |

FIG. 2B

| ☐ | PHYSICIAN 326 | 328 STD DEV FOR 30-DAY READMITS W/ EXCLUDES (SAME MS-DRG) | 330 CONTRIBUTION MARGIN | 332 ATTENDING REVENUE SHARE 334 EXPORT |
|---|---|---|---|---|
| ☐ | ○ PHYSICIAN A | -0.37σ | $1.16M | 100% |
| ☐ | ● PHYSICIAN B | 0.00σ | $1.54M | 99% |
| ☐ | ○ PHYSICIAN C | -0.14σ | $1.94M | 100% |
| ☐ | ○ PHYSICIAN D | -0.31σ | $865K | 99% |
| ☐ | ○ PHYSICIAN E | -0.25σ | $2.56M | 85% |
| ☐ | ○ PHYSICIAN F | 0.00σ | $1.15M | 100% |
| ☐ | ○ PHYSICIAN G | -0.29σ | $2.18M | 85% |
| ☐ | ○ PHYSICIAN H | -0.45σ | $2.82M | 89% |
| ☐ | ○ PHYSICIAN I | -0.25σ | $1.23M | 100% |
| ☐ | ○ PHYSICIAN J | 0.00σ | $1.53M | 100% |

10 RESULTS [10 ▼] 336

FIG.3C

| PHYSICIAN PERFORMANCE DASHBOARDS | | | | | |
|---|---|---|---|---|---|
| DR. MICHAELA QUINN | | | | | |
| • PERFORMANCE SUMMARY | | | | | |
| CI NETWORK SCORECARD 10 (of 12) | MEDICARE SHARED SAVINGS 12 (of 13) | LOS REDUCTION INITIATIVE 4 (of 4) | PQRS 9 (of 10) | QUALITY PHYSICIANS 9 (of 10) | HEALTHY HEART PROGRAM 8 (of 8) |
| 86TH PERCENTILE | 93RD PERCENTILE | 99TH PERCENTILE | 94TH PERCENTILE | | 99TH PERCENTILE |

| QUALITY OF CARE | STD DEV | TARGET | ACTUAL |
|---|---|---|---|
| % 30 DAY READMISSIONS (SAME FACILITY ANY APR DRG) | 0.27 | 9.01% | 7.52% |
| MORTALITY RATE O/E | N/A | 0.88 | 0.32 |
| % OF DISCHARGES W/ FOLLOW UP APPT WITHIN 7 DAYS | 0.4 | 80% | 87% |
| PERIOPERATIVE CARE (VTE) PQRS 23 | 0.13 | 80% | 95% |
| CAD LIPID CONTROL - PQRD #197/ACO #32 | 0.29 | 80% | 99% |

| COST AND UTILIZATION | STD DEV | TARGET | ACTUAL |
|---|---|---|---|
| AVG. CONTRIBUTION MARGIN PER IP CASE | 0.31 | $3,369 | $3,456 |
| AVG. COSTS PER IP CASE | 0.47 | $10,661 | $9,470 |
| AVG. LOB PER IP CASE | 0.22 | 2.18 | 3.65 |
| AVG. CONSULTANTS USED PER IP CASE | 0.89 | 1.3 | 1.2 |
| AVG. COSTS PER OP PROCEDURE | 0.31 | $403 | $384 |

| MARKET & LOYALTY | OPPORTUNITY | ACTUAL |
|---|---|---|
| INPATIENT REVENUE SHARE | 2% | 98% |
| OUTPATIENT REVENUE SHARE | 3% | 97% |
| TOTAL REVENUE | $65,933 | $2,571,403 |
| PAYER MIX (% COMMERCIAL % MEDICARE) | N/A | 64% |

FIG. 4A

| | | 3% |
|---|---|---|
| FREESTANDING FACILITY SHARE | | |
| REFERRAL SOURCES | | |

| PANEL MANAGEMENT | TARGET | ACTUAL |
|---|---|---|
| ATTRIBUTED EPISODE COUNT | 233 | 189 |
| AVERAGE COST PER EPISODE | $18,102 | $17,854 |
| RISK ADJUSTED AVERAGE COST PER EPISODE | $10,775 | $10,502 |
| % HIGH OUTLIER EPISODES | 3.5% | 3.1% |
| GENERIC UTILIZATION RATES | 95% | 96% |

| ACCESS & EFFICIENCY | TARGET | ACTUAL |
|---|---|---|
| AVG. TIME APPOINTMENT - NEW PATIENT | 7.2 DAYS | 5.4 DAYS |
| % NEW PATIENT ACCOMMODATED W/IN 14 DAYS | 90% | 93% |
| wRVUS | 11,699 | 11,836 |
| AVAILABLE CAPACITY | 5% | 19% |
| CARE NOTE TRANSMISSION % | 95% | 96% |

PHYSICIAN PERFORMANCE AND RECOMMENDATION INTERFACE

INTRODUCTION

Hospitals and physician networks often strive to acquire and retain the physicians that are of the highest-quality, while at the same time ensuring that the costs are controlled. Determining how to make effective choices to achieve that goal is often a highly-complex process. Health systems forming Accountable Care Organizations and other networks need tools to set strategy, analyze market data, measure performance on internal quality and regulatory programs, manage performance, and engage their clinicians. It is with respect to this general environment that embodiments of the present disclosure have been contemplated.

SUMMARY

In one aspect of the technology, a method for displaying physician analytics is provided. The method includes receiving a value metric and a quality metric for the physician. The value metric may represent a physician's value to a health system, whereas a quality metric represents the quality of care provided by the physician. Some examples of a value metric include a physician's contribution margin or the physician's revenue share. Some examples of a quality metric include 30-day readmission rate, mortality rate, complications of care, or any combination thereof. The value metrics and quantity metrics may also come from different sources, and may be selected or customized by the user.

A result metric for the physician may also be determined based on the value metric and the quality metric for the physician. That result metric may be displayed in multiple forms. For example, the result metric may be displayed on a chart, where one axis of the chart represents the value metric for the physician and the other axis of the chart represents the quality metric for the physician. In the example where the result metric is displayed on a chart, the result metric may be displayed as a physician indicator. The size of the physician indicator may be dependent on a quantity metric for the physician, which may also be received. The result metric may also be dependent on the received quantity metric.

Based on the result metric, insights for the physicians may also be determined. For example, the location of the physician indicator on a chart may indicate that a particular insight should be associated with the doctor. As an example, a physician may be considered a top contributor if the respective physician indicator is in the corresponding segment of the chart. The insights may be displayed as a color of the physician indicator. For instance, one color or visual attribute of the physician indicator may correspond to a particular insight. An insight legend may be included in or adjacent to the chart to explain the insights and their relationship to the color or visual attribute of the physician indicator. Physician indicators for multiple physicians may also be displayed concurrently on the same chart.

Additional metrics and insights may also be provided for the physician upon selecting a physician indicator from the chart. Upon selecting the physician indicator, a physician performance analysis may be presented that includes various metrics and information regarding the particular physician that corresponds to the physician indicator that was selected.

In another aspect of the technology, a referral recommendation may also be made for a physician. The recommendation may be based on the result metric for the physician. For example, the rank of a physician in a results list for referrals may be adjusted based on the physician's result metric.

In all cases, the technology disclosed herein is intended to be used subject to all applicable laws of the pertinent jurisdiction. These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

There are shown in the drawings, embodiments of the disclosure, it being understood, however, that the disclosure is not limited to the precise arrangements and instrumentalities shown.

FIGS. 2A-B depict an exemplary process flow for providing a physician performance interface.

FIGS. 3A-3D depict embodiments of a physician performance interface.

FIGS. 4A-B depict an embodiment of a physician performance analysis.

DETAILED DESCRIPTION

Embodiments of the present disclosure relate to a methods and systems for provided analysis, insights, and recommendations for physicians within a health system. A health system includes any environment in which physicians have some relationship to one another by virtue of a relationship to another entity, such as a hospital, network of hospitals, or physician network. The embodiments of the present disclosure also provide for user interfaces to display information about physicians and allow users to interact with the user interface.

Figure 1:
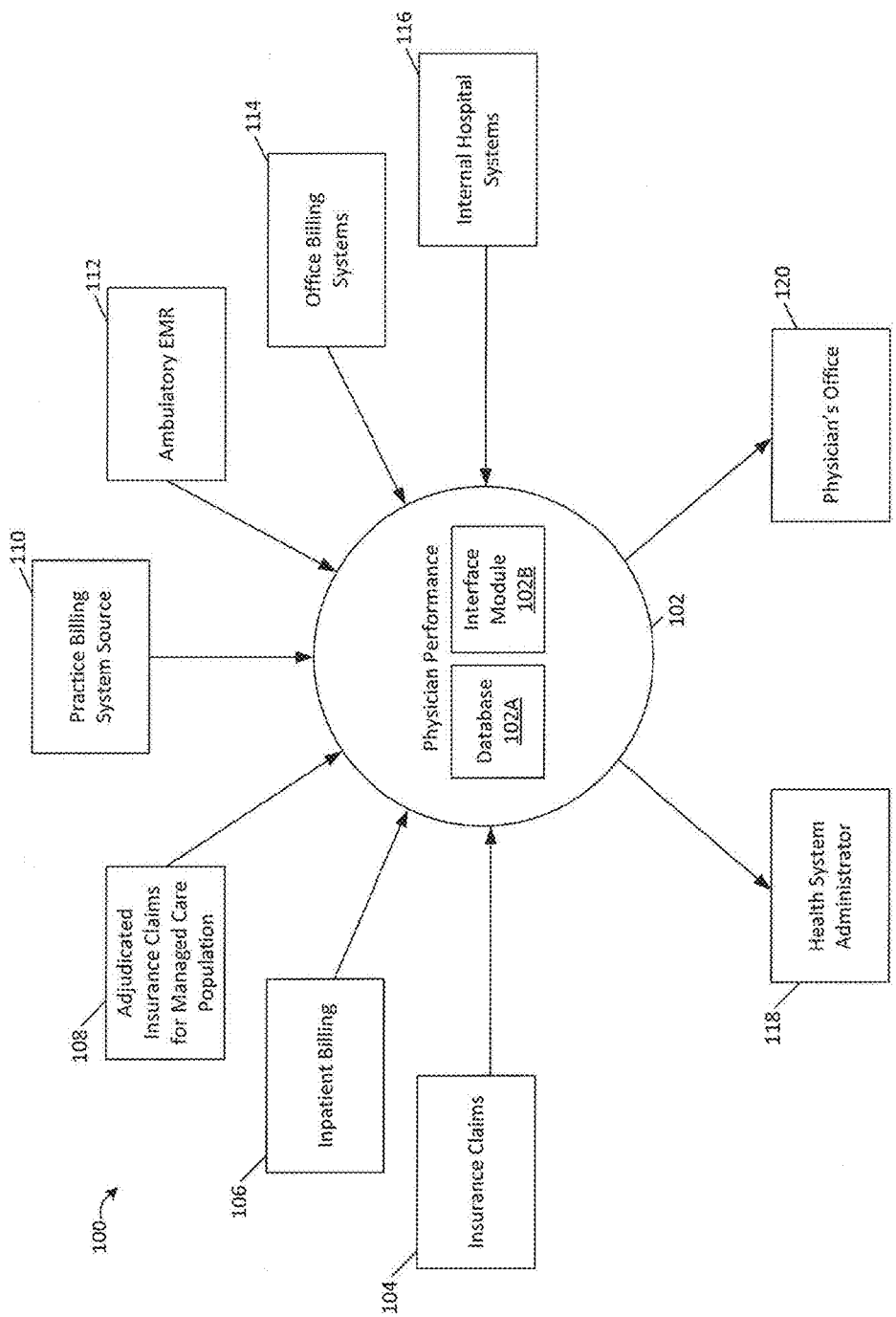
FIG. 1 depicts a system for implementing a physician performance interface, in accordance with embodiments of the invention.

FIG. 1 depicts a system 100 for implementing a physician performance interface. As depicted, a physician performance computing system 102 receives data from multiple different sources. The physician performance computing system 102 may be implemented as a standalone or may be functionally integrated into a health system administrator system 118 or a physician's office system 120, or any combination thereof. The physician performance computing system 102 receives information from one or more insurance claims sources, collectively referred to herein as an "insurance claims source" 104. The insurance claims source 104 may provide information about physician market data, such as shares and relationships, among other things. For instance, the insurance claims source may provide information including inpatient and outpatient revenue shares along with total revenue. Inpatient and outpatient volumes and volume shares may also come from this source, in some embodiments. Payer mix information, such as the percentage of commercial insurance versus Medicare, for physicians may come from this source as well. The insurance claims source 104 may also provide information regarding a freestanding, ambulatory, hospital or non-hospital facility share and referral sources. In addition, the insurance claims source 104 may also provide information regarding referring physicians who have shared patients over a specific time period. The insurance claims source 104 may be, at least in part, the Crimson Market Advantage® product available from The Advisory Board Company of Washington, D.C. or data therefrom.

The physician performance computing system 102 also receives data from one or more inpatient billing data sources, collectively referred to herein as "an inpatient billing data source" 106. The inpatient billing data source 106 may also include information from provider charge data. The inpatient billing data source 106 may provide information from which quality metrics for physicians can be derived. For instance, the quality metrics information derived from provider charge data may include readmission rates, such as the percent of readmissions within 30 days. The mortality rate for physicians may also be provided as well as the percentage of discharges that have a follow-up appointment within seven days. Other quality metrics such as preoperative care (e.g., venous thromboembolism prophylaxis) and coronary artery disease (CAD) lipid control may be provided by the inpatient billing data source 106 (or derived from provider charge data provided by the inpatient billing data source 106). In addition, other quality metrics may include the percentage of three-day readmissions, the percentage of seven-day readmissions, the percentage of 30-day readmissions, complications of care, complications of condition, inpatient quality indicators, patient safety indicators, pediatric quality indicators, cases with hospital acquired conditions, complications of care/expected ration, core measures, hospital acquired conditions observed/expected ratio, mortality observed/expected ratio, mortality rate, percent of readmissions, and top complications of care, among others. The inpatient billing data source 106 may comprise, at least in part, the Crimson Continuum of Care® product available from The Advisory Board Company of Washington, D.C., or data therefrom.

The physician performance computing system 102 also receives data from one or more adjudicated insurance claims for managed care population sources, collectively referred to herein as an "adjudicated insurance claims for managed care population source" 108. The adjudicated insurance claims for managed care population source 108 provides comprehensive longitudinal data for a specific patient population from which information about population costs and efficiencies may be derived. The adjudicated insurance claims for managed care population source 108 may also provide additional information about population-based quality metrics in addition to the quality metrics data potentially received from other sources. For example, the information from the adjudicated insurance claims for managed care population source 108 may include attributed episode counts, average costs per episode, risk adjusted average costs per episode, percentage of high outlier episodes, and generic utilization rates. The adjudicated insurance claims for managed care population source 108 may comprise, at least in part, the Crimson Population Risk Management® product available from The Advisory Board Company of Washington, D.C., or data therefrom.

The physician performance computing system 102 further receives data from the practice billing system source 110 for example by intercepting outgoing claims. The practice billing system source 110 provides information regarding ambulatory quality metrics such as Physician Quality Reporting System (PQRS) metrics, Healthcare Effectiveness Data and Information Set (HEDIS) metrics, and e-prescribing data. The practice billing system source 110 may comprise, at least in part, the Crimson Continuum of Care® Ambulatory Module product available from The Advisory Board Company of Washington, D.C., or data therefrom.

The physician performance computing system 102 also receives data from another ambulatory EMR source 112 that provides information about risk prediction. The risk prediction information may be derived from both the data within the ambulatory EMRs along with the free text notes within the ambulatory EMRs. The ambulatory EMR source 112 may comprise, at least in part, the 360Fresh™ product available from The Advisory Board Company of Washington, D.C., or data therefrom.

The physician performance computing system 102 also receives data from one or more practice management sources, collectively referred to herein as a "practice management source" 114. The practice management source 114 provides information about physician office productivity and efficiency metrics. For instance, the information may include average time for an appointment for a new patient, and the percentage of new patients accommodated within fourteen days. Other information may include available capacity, patient access, and work relative value units (wRVUs) for physicians. An RVU is the relative level of time, skill, training, and intensity to provide a given service and work is the portion of reimbursement associated with the physician's work. The practice management source 114 may comprise, at least in part, the Crimson Medical Group Advantage™ product available from The Advisory Board Company of Washington D.C., or data therefrom.

Yet another source for the physician performance computing system 102 is an internal hospital systems source 116, which may be comprised of multiple underlying sources. The internal hospital systems source 116 provides information about hospital related activities such as cost of supplies and utilization of the operating room. For example, the information may include average contribution margin per case, average costs per case, average Length of Stay (LOS) per inpatient, and the average consultants used per case. The internal hospital systems source 116 may comprise, at least in part, the Crimson Surgical Profitability Compass® product available from The Advisory Board Company of Washington D.C., or data therefrom.

The data and information provided by each of the sources may also be categorized by a particular health system. For example, all data relating to physicians in a particular health system, such as a physician network or a hospital, may all be grouped together or designated as such. In some embodiments, indicating a physician's health system may be accomplished by including metadata tags for all information that is received by the physician performance computing system 102. The physician performance computing system 102 may perform additional analysis to classify or categorize the data and information based on the health system of the physician.

In some embodiments, upon receipt of at least some of the information and data provided by the data sources, the physician performance computing system 102 may store the data in a database 102A within the physician performance computer system. In other embodiments, each of the data sources continues to house the data separately and application programming interfaces (APIs) or other transfer mechanisms are utilized to share data between data sources and the physician performance computing system 102. The physician performance computing system 102 may also determine whether the data requires further processing and analysis prior to being utilized in a physician performance interface for a physician referral interface. Where additional processing and analysis is required, the physician performance computing system 102 performs the processing and data analysis. The analysis and processing may be performed by the interface module 102B within the physician performance computing system 102. In some embodiments, the sources and the physician performance computing system 102 are integrated into a single computing system. In other embodiments, at least some of the sources are connected via a network, such as the Internet.

The physician performance computing system 102 utilizes the data to provide an interactive interface to a user computer, such as a computer utilized by health system administrator 118 or a computer at or accessible to a physician's office. The interfaces provided by the physician performance computing system 102 are discussed in additional detail below. Each of the systems and sources may be implemented separately by a computer system or server. The systems and sources may also be combined in one or more different combinations. Each of the systems and sources may all be communicatively coupled to the physician performance computer system 102, and one or more of the sources may communicate with each other as well.

Figure 2A:
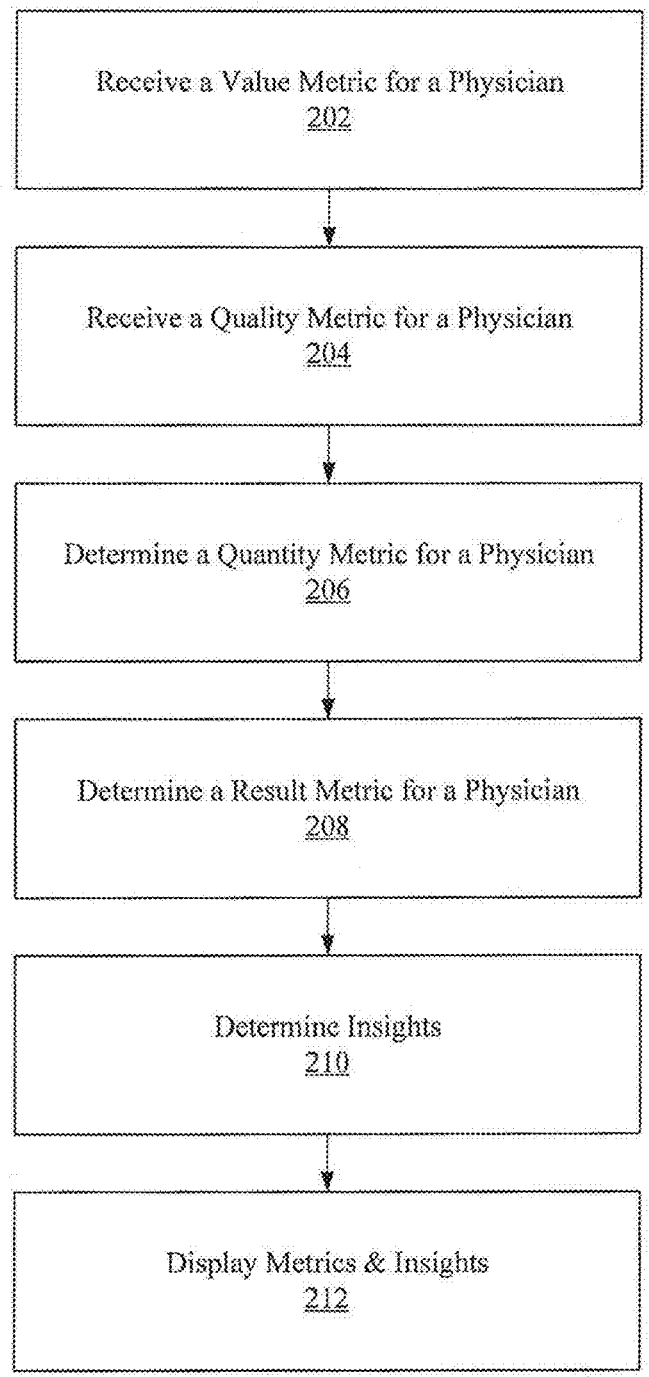

FIG. 2A depicts process flow for providing a physician performance interface. At operation 202, a physician performance interface component within the physician performance computing system receives a value metric for a physician. The value metric may include data relating to physician market data. The value metric may also indicate or relate the monetary value that a physician provides to a particular health system. For instance, the value metric may be the revenue share for a particular physician. The revenue share for a particular physician is the amount of the physician's revenue that is within the health system. The revenue share may be determined from the volume of claims for the physician and then converted to an expected revenue payment, from which the revenue share within the system may be determined. The revenue share may be further refined to be the inpatient revenue share or the outpatient share among other refinements. In embodiments, the value metric may be the contribution margin or volume for the physician. The contribution margin may be expressed as an amount equal to the revenue minus costs for the physician for the physician's procedures that is contributed. In other embodiments, the value metric is calculated from multiple types of value-related data and metrics. Other value metrics may include wRVUs, patient access, efficiency metrics, attributed episode counts, average costs per episode, risk adjusted average costs per episode, per member per month costs, and generic utilization rates. Receiving the value metric may include receiving the value metric from the sources depicted in FIG. 1. In other embodiments, receiving the value metric may be an interface module receiving the value metric from a database within the physician performance computing system.

The particular type of value metric, or the underlying data defining the value metric, may be selected or customized via user input. For example, user input may indicate a particular type of value metric that is preferred. The user input may be in the form of a selection of a preset group of metrics to provide specific insights for a set of physicians.

A quality metric is received for a physician at operation 204. The quality metric may include data relating to the quality of care provided by the physician. In some embodiments, the quality metric may be derived from other underlying data as well. For example, the quality metric may be a weighted quality score. The weighted quality score may be based on underlying data, such as mortality rate, complications of care rate, and the 30-day readmission rate. In embodiments, a specific weighted quality score, a "Z-score", may be used. The Z-score is a score weighted as follows: 50% weight to the 30-day readmission data, 30% weight for the mortality rate, and 20% weight to the complications of care rate. Other examples of quality metrics include percentage of three-day readmissions, the percentage of seven-day readmissions, the percentage of 30-day readmissions, complications of care, complications of condition, inpatient quality indicators, patient safety indicators, pediatric quality indicators, cases with hospital acquired conditions, complications of care/expected ration, core measures, hospital acquired conditions observed/expected ratio, mortality observed/expected ratio, mortality rate, percent of readmissions, and top complications of care, among others. Physician Quality Reporting System (PQRS) metrics, Healthcare Effectiveness Data and Information Set (HEDIS) metrics, and e-prescribing data may also be utilized. Additionally, quality metrics such as percentage of high outlier episodes, evidence-based compliance, immunization records, avoidable admissions, avoidable emergency department visits, and patient risk, may also be used. Similar to the value metric, the quality metric, or the underlying data defining the metric, may be selected or customized via user input. As such, the health system administrator, or another user, has the ability to customize what the user would like to see as a quality metric. Receiving the quality metric may include receiving the quality metric from the sources depicted in FIG. 1. In embodiments, receiving the quality metric may be an interface module receiving the quality metric from a database within the physician performance computing system 102.

A quantity metric for a physician may also be received at operation 206. The quantity metric may be based on data such as the number the physician's patients, the physician's case volume, the number of operations, or other similar quantity-based metrics for the physician. The quantity metric may also be the revenue share, revenue, volume, or other related data for the physician. The quantity metric may also be selected or customized via user input, similar to the value metric and the quality metric. Receiving the quantity metric may include receiving the quantity metric from the sources depicted in FIG. 1. In embodiments, receiving the quantity metric may be an interface module receiving the quantity metric from a database within the physician performance computing system 102.

At operation 208, a result metric is determined for the physician. In embodiments, the result metric is determined based on at least the value metric and the quality metric received at operation 202 and operation 204, respectively. The result metric may also be further based on the quantity metric. For instance, the result metric may be represented by a coordinate or a one-by-two matrix entry in a database, wherein the two values in the entry are the value metric and the quality metric. In embodiments, the result metric is determined via an algorithm based on the value metric and the quality metric. For instance, the value for the value metric and the value for the quality metric may be mathematically combined, e.g., added or multiplied, to receive a single value. The result metric may also be based on additional user input concerning how the result metric should be determined from the value metric and the quality metric. In embodiments, the result metric may be based on additional underlying data points in addition to the data utilized in the value metric and the quality metric. For instance, the result metric may be a combination of (1) the number of standard deviations the physician's quality metric is from the mean quality metric of all the other physicians within a particular health network and (2) the percentage of revenue share of the health system for the physician. In embodiments, the result metric may be a combination of (1) the number of standard deviations for a 30-day readmission rate and (2) the physician's contribution margin. In embodiments, the result metric may also be a combination of (1) the value metric of wRVUs for a physician and (2) the quality metric of readmission rate for the physician. In embodiments, the result metric may be a combination of (1) the patient access value metrics for the physician and (2) the quality metric of emergency department visits.

At operation 210, an insight for the physician is determined. In embodiments, the insight for the physician is an insight for use by the health system for how to handle the physician. For instance, an insight may be related to helping increase the profile of a particular physician with other physicians within the health system. Additionally, insights may include types of training that the particular physician should receive. The insight may be determined based on the result metric. For example, on the one hand, if the result metric is lower than the average result metric for physicians in a health system, the physician may need additional training. On the other hand, a physician that has an above average result metric may be considered a top contributor or valuable member to the health system. The particular insights, however, may change when the type of value metric and the type of quality metric are changed. The insights may also be dependent on additional factors, such as physician attributes (also referred to as physician facts), such as if the physician is currently employed. For example, if the physician is unemployed, the insight may indicate to hire the physician if the other metrics utilized in determining the insight are positive. If the physician is employed and has poor associated metrics, the insight may indicate that the physician is a low priority.

In embodiments, where the value metric is the revenue share for the physician and the quality metric is the Z-score for the physician, a set of insights may be made based on those two metrics combined as a result metric. For example, the revenue share may be a percentage between 0% and 100%. The Z-score may be represented as a number of standard deviations from the mean Z-score for physicians in the health system. A result metric may be determined as a graph coordinate or one-by-two matrix entry, as discussed above, which may be represented as [revenue share, Z-score]. The result metric may be considered, for example, in four segments for use in determining insights. The four segments may be represented by ranges as follows: (1) [>50%, >0], (2) [<50%, >0], (3) [>50%, <0], and (4) [<50%, <0]. An insight may be made based on the segment in which the physician's result metric falls. For example, if the result metric falls within range (1), the physician is a top contributor to the health system. If the result metric falls within range (2), the physician may be seen as growth opportunity. If the result metric falls within range (3), the physician may be viewed as a candidate for quality improvement who may need additional support. If the result metric falls within range (4), the physician may been seen as a low priority physician. Additional segments based on narrower ranges may be determined and additional insights provided based on the additional segments.

In embodiments, where result metric is based on the value metric of wRVUs for a physician and the quality metric of HEDIS metrics for the physician, the insights may be similar to those discussed above. For instance, a result metric indicating high wRVUs and high HEDIS metrics may correspond to an insight that physician is a top contributor. A result metric indicating high wRVUs and a low HEDIS metrics may correspond to an insight that the physician is a quality improvement candidate. A result metric indicating low wRVUs and a low HEDIS metrics may correspond to an insight that the physician is a low priority. A result metric indicating low wRVUs and a high HEDIS metrics may correspond to an insight that the physician has potential opportunity for improvement.

In embodiments, where the result metric may be a combination of the patient access value metrics for the physician and the quality metric of emergency department visits, the insights may also be similar to those above. For example, a result metric indicating high patient access metrics and low emergency department visits may correspond to an insight that the physician is a top contributor. A result metric indicating high patient access metrics and high emergency department visits may correspond to an insight that the physician is a low priority who may have potential quality issues. A result metric indicating low patient access metrics and high emergency department visits may correspond to an insight that patients are not being seen but are instead going to the emergency department, and the physician may need additional assistance and is a quality improvement candidate. A result metric indicating high patient access metrics and low emergency department visits may correspond to an insight that the physician is a potential growth opportunity because the physician is not seeing many patients.

In another example, the result metric may be a combination of the risk adjusted average costs per episode value metric and the quality metric of avoidable admissions. In that example, the insights may be similar to those discussed above. For instance, a result metric indicating low risk adjusted average costs per episode and low avoidable admissions may correspond to an insight that physician is a top contributor. A result metric indicating low risk adjusted average costs per episode and high avoidable admissions may correspond to an insight that the physician is a quality improvement candidate. A result metric indicating high risk adjusted average costs per episode and low avoidable admissions may correspond to an insight that the physician has a potential opportunity for improvement. A result metric indicating high risk adjusted average costs per episode and high avoidable admissions may correspond to an insight that the physician is a low priority.

In another example, the result metric may be a combination of per member per month costs and patient risk. Such a result metric would allow for insights that identify outliers. For instance, high risks are generally associated with high costs and low risks are associated with low costs. As such, where the result metric indicates that a physician has high per member per month costs and low patient risk metrics, the physician have a potential opportunity for improvement. Conversely, a result metric indicating that the physician has low per member per month costs and high patient risk metrics would correspond to an insight that the physician is a top contributor and a potential source for best practices.

The insight may also be based on a result metric incorporating the quantity metric. Such a result metric may be represented as a three-dimensional coordinate or a one-by-three matrix entry, such as [value metric, quality metric, quantity metric]. In some embodiments, each metric may be represented by the number of standard deviations from the mean. In such embodiments, the insights may be based on whether each metric is above or below average. Similarly, the insights may also be based on whether each metric is above or below a threshold. For example, the insight could be based on whether a physician contributes more or less than one-million dollars. With that type of basis for insights, eight possible insights may be created as shown in FIG. 2B. Additional insights may be created through additional segmentation of ranges for each of the values.

Returning to FIG. 2A, at operation 212, the metrics and insight for the physician are displayed. In embodiments, the value metric, the quality metric, and the quantity metric may each be displayed along with the insight for the physician. In embodiments, only a subset of the metrics or the insight may be displayed. In an example embodiment, the metrics and insights may be displayed on a graph, chart, or plot. In certain embodiments, the y-axis of the chart may be representative of the value metric and the x-axis may be representative of the quality metric, or vice versa. A physician indicator (also referred to herein as "indicator") may be displayed at the appropriate position or coordinate representing the physician's result metric. Additionally, in embodiments, the size of the physician indicator may also represent the quantity metric or correlate with the value of quantity metric. The color, texture, or another feature (e.g., a visual feature) of the physician indicator may also represent the insight for the physician. A legend may also be displayed, where the legend provides the relationship and/or definition of the colors, textures, or other features of physician indicators correspond to particular insights. Additionally, the physician indicator may be displayed among other physician indicators. The other physician indicators may represent the metrics and insights for other physicians associated with the health system. Embodiments of interfaces utilized to display the metrics and insights are discussed below. Additional display methods may also be utilized, such as three-dimensional charts wherein each dimension represents a separate metric. For example, the x-axis may represent the quality metric, the y-axis may represent the value metric, and the z-axis may represent the quantity metric.

Figure 3A:
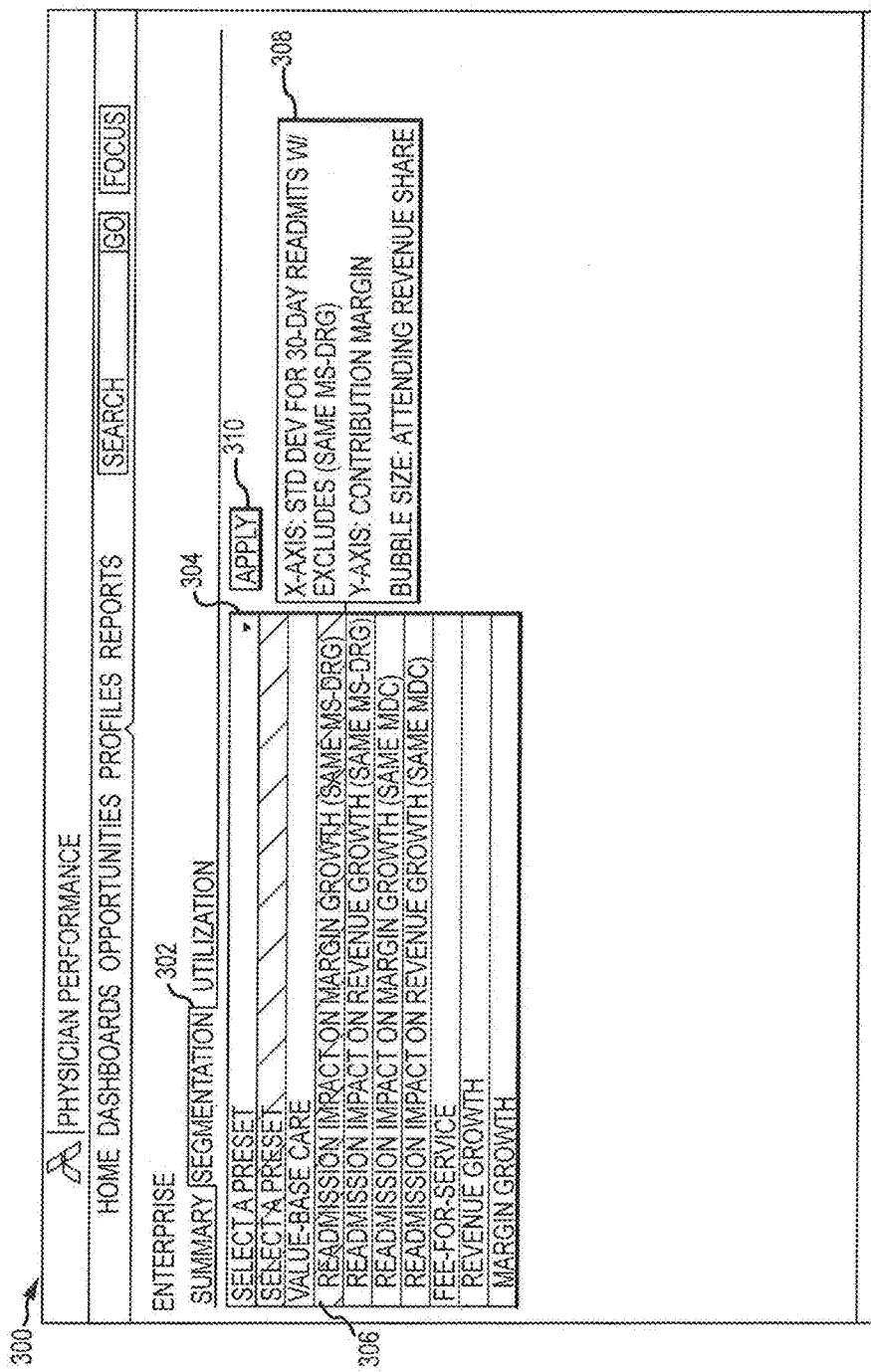

FIG. 3A depicts a user interface 300 for selecting and customizing the metrics to be displayed in a physician performance user interface. The user interface 300 may include the display of elements within a window in a computing display. The user interface 300 includes several tabs for selection by the user, including a segmentation tab 302. Upon receiving a selection of the segmentation tab 302, the user interface 300 displays a button 304 for selection of preset metrics to be displayed. Upon receiving a selection of the button 304, a drop-down list 306 with multiple presets is displayed. The multiple presents in the drop-down list 306 represent different preset options for physician performance analytics that a user may select. For instance, two categories are displayed in the drop-down list 306: Value-Based Care and Fee-For-Service. Within each of those categories are multiple preset options that may be selected. Each preset option defines which value metric, quality metric, and quantity metric will be utilized in the interface.

In embodiments of the invention, upon determining that a selection device is hovering on, or has selected, a particular preset, a pop-up box 308 or other graphical user interface window is displayed in the user interface 300. The pop-up box 308 displays the metrics that will be displayed in the user interface, including the value metric, the quality metric, and the quantity metric. For example, in the example depicted in FIG. 3A, upon detecting a selection device hovering above the preset "Readmission Impact on Margin Growth," the pop-box 308 displays that the quality metric will be displayed on the x-axis and will be the standard deviation for the 30-day readmission rate for physicians. The pop-up box 308 also indicates that the value metric will be displayed on the y-axis and will be the contribution margin for physicians. The pop-up box 308 further indicates that the quantity metric will be represented by the bubble size of the physician indicator and will be the attending revenue share for the physicians. Upon selection of a preset, the drop-down list 306 collapses displaying the selected preset. Upon selection of the apply button 310 after a selection of a present, a graphical representation of the metrics is displayed in the user interface 300, as depicted in FIG. 3B and discussed below.

In embodiments, a selection interface, such as a drop down list, may be provided for each of the metrics. For instance, a first selection interface may be provided for selection of the value metric, a second selection interface may be provided for selection of the quality metric, and a third selection interface may be provided for selection of the quantity metric. Upon selection of the apply button 310, a graphical representation of the selected metrics may be displayed. Those of skill in the art will appreciate that other options are possible for receiving selection of the metrics.

Figure 3B:
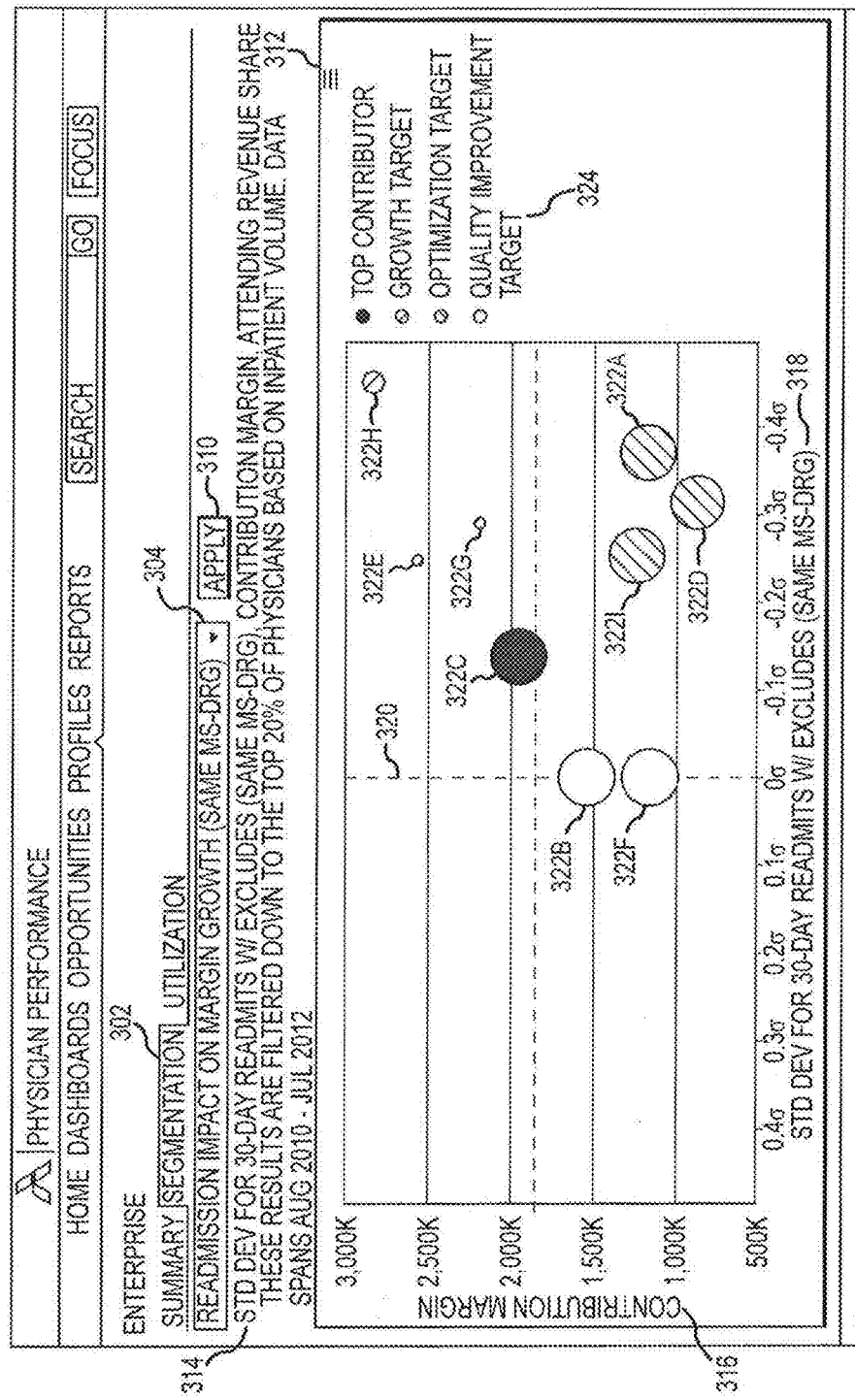

FIG. 3B depicts an example of a user interface for displaying the metrics and insights for physicians. As depicted in FIG. 3B, the user interface includes a physician analysis chart 312 that displays the metrics and insights for physicians based on the selection of a preset from the drop-down list 306. The value metric is represented on the y-axis 316 and the quality metric is represented on the x-axis 318 of the chart 312. A title 314 above the chart 312 states the metrics involved along with other potential information or caveats concerning the basis of the metrics. The value metric represented on the y-axis 316 may have an appropriate scale depending on the metric represented. For example, as depicted in FIG. 3B, the value metric represented on the y-axis 316 is the contribution margin of a physician. As such, the scale for the y-axis 316 is in thousands of dollars. The quality metric represented on the x-axis 318 may also have an appropriate scale. As depicted in FIG. 3B, the quality metric represented on the x-axis 318 the standard deviation for the 30-day readmission rate. As such, the scale for the x-axis 318 is the number of standard deviations from the mean, where the center of the x-axis 318 indicates zero standard deviations, or the average 30-day readmission rate. In the particular example depicted in FIG. 3B, the number of negative standard deviations (indicating a less-than-average 30-day readmission rate) is shown to the right of center of the x-axis 318. The negative standard deviations are shown to the right because, traditionally, more positive results are shown to the right of center, and having a lower 30-day readmission rate is a positive quality for a physician.

Within the chart, multiple physician indicators 322A-I are displayed along with a segmentation indicator 320 and an insight legend 324. Each of the physician indicators 322A-I are positioned on the chart 312 at a coordinate corresponding to the physician's result metric. As depicted, each of the physicians represented by physician indicators 322A-I have different result metrics, as represented by the different locations of the physician indicators 322A-I. For example, the physician represented by physician indicator 322H has a value metric that is higher than the value metric for any other physician. The physician represented by physician indicator 322H also has a lower 30-day readmission rate than any of the other physicians represented in the chart 312.

The size of the physician indicators 322A-I represented the quantity metric for the physician. In the example depicted in the FIG. 3B, the quantity metric is the revenue share for a particular physician. Where the physician has a higher associated revenue share, the corresponding physician indicator will be larger than that of a physician with a smaller revenue share. For example, as depicted in FIG. 3B, the physician represented by physician indicator 322H has a smaller revenue share than the physician represented by physician indicator 322I. The size of the bubble may be proportional to the difference of the physician with the lowest value for a quantity metric and the physician with the highest value for the quantity metric. For instance, the physician represented by physician indicator 322E may have a revenue share value of 85%, and the physician represented by physician indicator 322I may have a revenue share value of 100%. Even though there is only a 15% difference between the two physician indicators, the bubble size of the physician indicator 322I is substantially bigger than the physician indicator 322E because the size is relative to the 15% difference.

The insights determined for the physicians are also displayed. As depicted in FIG. 3B, the insights for the physicians are displayed as different textures or colors of the physician indicators 322A-I. An insight legend 324 is displayed in chart 312. The insight legend 324 shows the correlation between textures or colors and insights. In the example depicted in FIG. 3B, there are four separate insights provided for the physicians represented in the chart 312. The four insights in the illustrated example provide insight as to whether the physician is a top contributor, a growth target, an optimization target, or a quality improvement target. The insights in the illustrated example are based on a result metric that is based on the value metric, the quality metric, and the quantity metric. For example, the physician represented by physician indicator 322G has a provided insight that the physician is a growth target, in part, because the physician an above average quality metric and an above average contribution margin, but has a small associated revenue share. The physician represented by physician indicator 322F has an insight that the physician is a quality improvement target, in part because the physician has a below average quality metric.

FIG. 3C depicts another element of the user interface for displaying physician performance analysis. As depicted in FIG. 3C, a table including information about physicians' metrics is displayed. The metrics displayed in the table are the same metrics that were represented in the chart 312 in FIG. 3B. As such, in some embodiments, the chart in FIG. 3C may be displayed below the chart 312. A user may be able to scroll down in the window to see the table below the chart. In embodiments, the table may be displayed on a separate page or in a separate window. The table displays a list of the physicians' names or other identifiers of physicians are shown in the first column 326. In the second column 328, the value metric is displayed. In the third column 330, the quality metric is displayed. In the fourth column 332, the quantity metric is displayed. For example, in the example depicted in FIG. 3C, the value metric is the standard deviation for the 30-day readmission rate for a particular physician, the quality metric is the contribution margin for the particular physician, and the quantity metric is the revenue share for the physician. Those metrics correspond to the same metrics represented in the chart 312 of the example depicted in FIG. 3B. Other arrangements of the data shown in FIG. 3C are possible.

The physicians listed in column one 326 of the table correspond to physicians displayed in the chart 312 depicted in FIG. 3B. The table also displays the corresponding values for the metrics of the physicians. For example, as shown in the table, Physician H has a value metric of $-0.45\sigma$, a quality metric of $2.82M, and a revenue share of 89%. As such, Physician H corresponds to the physician represented by physician indicator 322H in chart 312 in FIG. 3B. In addition to the values of the metrics shown in the table, the insights for the physicians are also represented in the table. Next to each of the physicians' names in the first column 326 is a circle with the same coloring or texture as the corresponding physician indicator 322A-I in chart 12.

The user interface further includes a results number control 336. The results number control 336 allows a user to view a particular number of results. Upon selection of the results number control 336, a drop-down list may be displayed listing the possible number of results to display.

Also included in the user interface may be an export button 334. The export button 334 allows a user to export data or results from the user interface. For example, a user may check the boxes next to the names of the physicians for which the user desires to export results. Upon selection of the export button 334, the values for the metrics for the selected physicians are exported, for example to a separate spreadsheet or to another application or storage location. In embodiments, a chart similar to the chart 312 will also be exported with the physician indicators corresponding to the selected physicians being displayed in the exported chart.

Figure 3D:
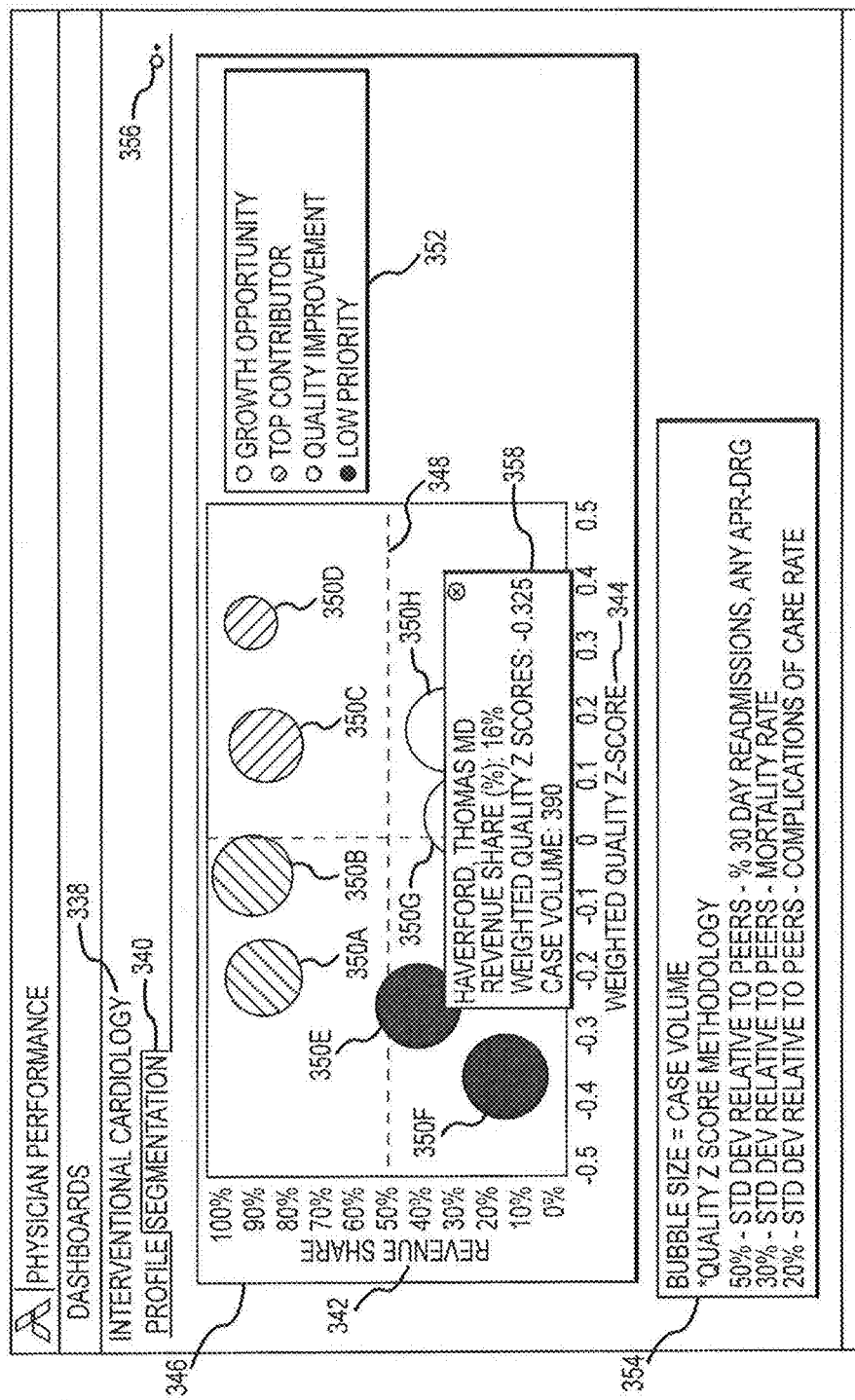

FIG. 3D depicts another example of a user interface for displaying physician performance analytics. A physician analysis chart 346 is depicted in FIG. 3D. The chart 346 is similar to the chart 312 from FIG. 3B, and the chart 346 displays the physician indicators 350A-H. The y-axis 342 of chart 346 represents a value metric for physicians and the x-axis 344 of the chart 346 represents a quality metric for physicians. In embodiments where the value metric is revenue share and the quality metric is a Z-score for the physician, as depicted in FIG. 3D, the quality metric scale may be based on the number of standard deviations from the mean Z-score for all physicians in the health system. In the illustrated example, the middle of the scale on axis 344 would indicate the mean, i.e., zero standard deviations from the mean. Left of the center of the axis 344 is representative of Z-scores that are less than the mean Z-score, and right of the center of the axis 344 is representative of Z-scores that are higher than the mean Z-score. For the value metric axis 342, the center of the axis represents a 50% revenue share, with values higher than 50% being above the center of the value metric axis 342. Therefore, the physician represented by the physician indicator 350A has a revenue share metric that is higher than 50%, but the physician's Z-score is below average.

The size of the physician indicators 350A-H represent a quantity metric for a physician. In embodiments, the quantity metric is the case volume for a physician. In embodiments, the chart indicates that the physician represented by physician indicator 350C has a larger case volume than the physician represented by physician indicator 350D, but a smaller case volume than the physician represented by physician indicator 350F. For example, the physician represented by physician 350F has a high case volume, but a low quality metric and a low revenue share.

A key 354 may also be displayed in or near the chart 346. The key 354 may display additional information about the metrics that are represented in the chart 346. For instance, the key 354 may indicate how the quantity metric is displayed. As depicted in FIG. 3D, the key 354 notes that the bubble size is representative of the quantity metric, which is the case volume for the example depicted. In the depicted example, the key 354 also displays the methodology for calculating the Z-score that is used as the quality metric. Specifically, the key 354 shows that the Z-score is a weighted score based on the 30-day readmission rate, the mortality rate, the complications of care rate for a physician.

Insights for the physicians are also displayed. As depicted in FIG. 3D, the insights for the physicians are displayed as different textures or colors of the physician indicators 350A-H. An insight legend 352 is displayed in or near the chart 346. The insight legend 352 shows the correlation between textures or colors and insights. In the example depicted in FIG. 3D, there are four separate insights provided for the physicians represented in the chart 346. As depicted, one insight determined may be that a physician is a growth opportunity and there should be a recruiting focus. Another insight is that a physician is a top contributor. Yet another insight is that a physician is a candidate for quality improvement and may require support. Still another insight is that a physician is a low priority. These insights may be based on the segment of the chart 346 in which the corresponding physician indicator is located. For instance, all physician indicators in the upper left-hand segment, as defined by the segment indicators 348, are considered to be quality improvement candidates, whereas all physician indicators in the upper right-hand segment may be considered all to be top contributors. Additional segments may be displayed in embodiments and additional insights that are based on additional segments may also be provided.

In user interface depicted in FIG. 3D, the physician's name associated with a physician indicator may also be displayed as well as the actual values for the quality metric, value metric, and quantity metric. In embodiments, upon a detection that a selection device, such as appointing device is hovering over a physician indicator, a pop-up box 358 or interface window containing the physician's name associated with a physician indicator, the value for the quality metric, the value for the value metric, and the value for the quantity metric. In embodiments, a selection device may comprise a pointing device such as a mouse pointer, a stylus, a user's finger when using a touch-input device, etc. In embodiments, the pop-up box 358 is also displayed upon a selection of a physician indicator. In some embodiments, all or some of the information displayed in pop-up box 358 may be displayed directly in the physician indicator. As depicted in FIG. 3D, upon detection of selection device hovering above physician indicator 350F, the pop-up box 358 is displayed. The pop-up box 358 displays the name of the name of the physician, here—Thomas Haverford MD, associated with physician indicator 350F. Also displayed in the pop-up box 358 are the values for the value metric, quality metric, and quantity metric associated with Thomas Haverford. In the example depicted, Dr. Thomas Haverford has an associated revenue share value of 16%, a Z-score that is 0.325 standard deviations less than the mean, and a case volume of 390.

In some embodiments, upon a selection of the physicians name in the pop-up box 358, a new page with additional information on the physician may be displayed. The additional information may also be displayed upon selection of the physician indicator itself. The additional information may be compiled and displayed as a physician performance analysis, as depicted in FIGS. 4A-4B and described below. In embodiments, the additional information includes additional value metrics, quality metrics, and quantity metrics.

FIGS. 4A-B depict an example of a physician performance analysis 400. In embodiments, the physician performance analysis 400 is primarily for a single physician. The physician performance analysis may be accessed, for example, from the user interface 346 as discussed above by selecting a physician indicator or a physician name in a pop-up box or interface window. The physician performance analysis may also be accessed by searching for a physician or by selecting a physician from another user interface. The name of the physician is displayed in the title block 402. In the depicted example, the particular physician for whom the performance analysis relates is Dr. Michaela Quinn.

A performance summary 404 is provided for the physician in the physician performance analysis 400. The performance summary 404 provides an overview of the physician's performance. In some embodiments, the performance summary 404 includes scores or rankings, such as rankings based on aggregate quality or quantity scores, for the physician across different categories. In the example depicted in FIG. 4A, five separate ranks for Dr. Michaela Quinn are included in the performance summary 404. One exemplary ranking is the physician's clinically integrated (CI) network scorecard in a section 406 that indicates the physician's ranking against other physicians in the CI network. Another ranking is the Medicare shared savings ranking in a section 408. Another ranking is the length of stay reduction initiative in a section 410. Yet another ranking is the PQRS quality physicians ranking in a section 412. Still another ranking is the healthy heart program rating in a section 414. The rankings may be initiatives that the health system is tracking against. Any number of rankings may be incorporated in the physician performance analysis 400, subject to applicable law. In embodiments, these rankings may also be omitted from the physician performance analysis 400.

Following the performance summary may be a more detailed view of metrics associated with the physician. The displayed metrics may be arranged into different categories or sections. For example, as depicted in FIG. 4A-B, there are five separate sections: a quality of care section 416, a cost and utilization section 418, a market and loyalty section 420, a panel management section 422, and an access and efficiency category 424. Within each section, metrics that are associated with each category are displayed for the physician. For example, quality of care metrics may include metrics such mortality rate and the percentage of 30-day readmissions; costs and utilization metrics may include average costs and average contribution margin per inpatient case and the average; market and loyalty metrics may include total revenue and different revenue shares; panel management metrics may include utilization rates and average costs per episode; and access and efficiency metrics may include average time for a new patient appointment and available capacity for a physician. In embodiments, such quality of care metrics, among others, may be used in determining the quality metric calculated and displayed in the charts discussed above with respect to FIGS. 3A-D. Similarly, the cost and utilization metrics and market and loyalty metrics, among others, may be used in determining the value metric calculated and displayed in the charts discussed above with respect to FIGS. 3A-D.

Multiple values for each of the metrics may also be displayed. In some embodiments, the physician's actual value for the metric, the target value for the metric, and the physician's standard deviation from the mean may all be displayed. In the example depicted in FIGS. 4A-B, the actual value for the metrics is displayed in an actual value column 430, the target value for the metric is displayed in a target value column 428, and the number of standard deviations value is displayed in the standard deviation column 426.

Figure 5:
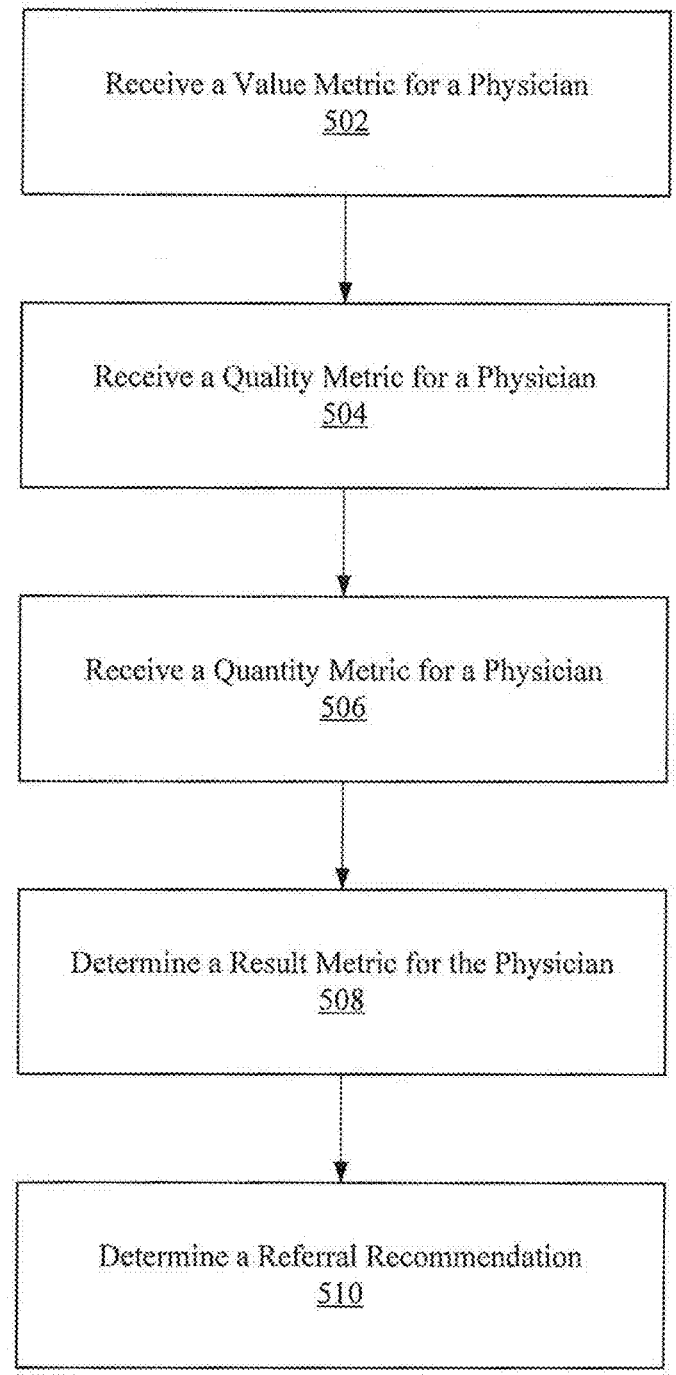
FIG. 5 depicts an exemplary process flow for determining a referral recommendation.

FIG. 5 depicts a process flow for making a referral recommendation for a physician. At operation 502, a value metric is received for a physician. The value metric may be any of the value metrics described above. At operation 504, a quality metric is received for the physician. The quality metric may be any of the quality metrics described above. At operation 506 a quantity metric may be received. The value metric, quality metric, and quantity metric may be selected or customized via user input, subject to applicable law. Receiving the metrics may include receiving any combination, in any order of the value metric, the quality metric, and/or the quantity metric from the sources 104, 106, 108, 110, 112, 114, 116 depicted in FIG. 1. In embodiments, receiving the metrics may also comprise an interface module 102B receiving the metrics from a database 102A within the physician performance computing system 102.

Based on the value metric and the quality a metric (and in some embodiments the quantity metric), a result metric is determined at operation 508. The result metric may be any of the result metrics discussed above and may be determined by any of the methods discussed above.

At operation 510, a referral recommendation is determined for the physician, subject to applicable law. When a physician or a health system needs to refer a patient to another physician, it is useful to have recommendations on whether or not a certain physician is recommended. The referral recommendation determined in operation 510 provides a recommendation concerning the preference in recommending a particular physician. For instance, where a user enters a physician's name into a user interface as a possible candidate for a referral, the user interface may provide the recommendation regarding the physician. In embodiments, the referral recommendation may also be integrated into search results for a physician referral. For example, a positive recommendation may increase the physician's ranking in a search results list, while a negative recommendation may decrease a physician's ranking in the search results list.

In embodiments, the referral recommendation is based on the result metric. The referral recommendation may also be based on particular segmentations or ranges of metrics, similar to the insights discussed above. The referral recommendation may also be determined via additional algorithms to determine a value representative of the recommendation. The value representative of the recommendation may then be incorporated into search algorithms for physician referrals.

Figure 6:
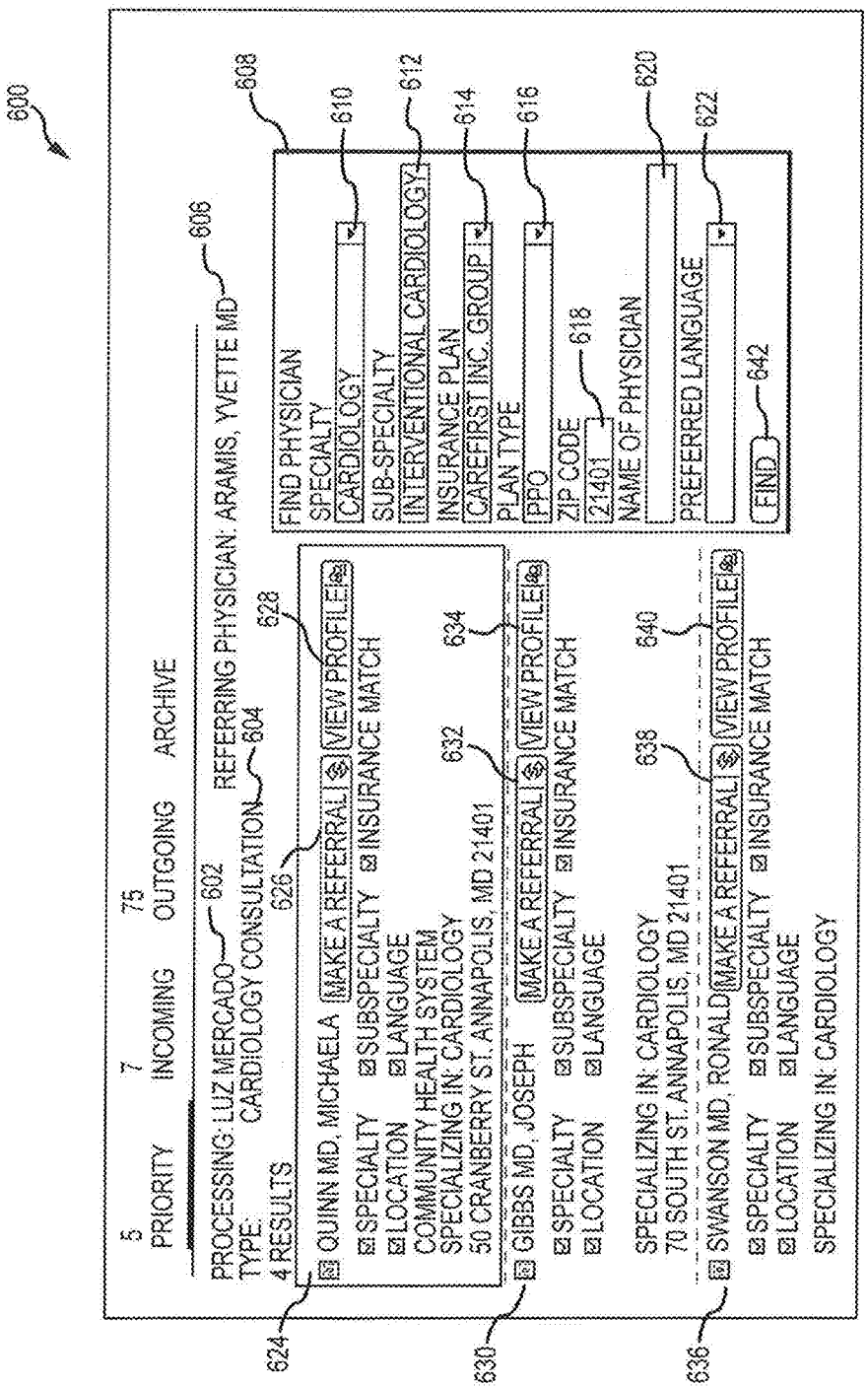
FIG. 6 depicts an embodiment of a referral interface.

FIG. 6 depicts an example of a referral interface 600 for receiving referrals based on referral recommendations. The referral interface 600 may include information regarding the patient 602, the referring physician 606, and the type of referral 604 that is being made.

As shown in FIG. 6, the referral interface includes a search component 608. The search component 608 receives user input to find a physician. Within the search component 608, there are several data entry fields or options for refining a search for a physician. In the depicted example, a specialty search list 610 is displayed. The specialty search list 610 allows a user to select a specialty for a referral physician. A sub-specialty option 612 may also be included to allow for search refinements by sub-specialty. An insurance plan option 614 and a plan type option 616 may also be included to allow for search refinements by insurance plan and insurance plan type. A geographic location-based option, such as a zip code option 618, may also be included to allow for search refinement by geographic area. A physician name search option 620 may be included to allow for a search refinement by the name of a physician. A preferred language option 622 option may be included to allow for search refinement by the languages spoken by a referral physician. Upon selection of the find button 642, a referral search is executed and a results list of physicians is displayed.

The results list contains entries for the referral physicians matching the search criteria according to a search algorithm. The referral physicians within the results list may be listed in sections containing additional information about the physician. For instance, as depicted in FIG. 6, three referral physicians were included in the results list: Michaela Quinn, Joseph Gibbs, and Ron Swanson. Each of the physicians has a different section with additional information about the physician.

In the Dr. Quinn section 624, the physician's name is displayed along with further information about Dr. Quinn. In embodiments, multiple checkboxes are displayed in the referral physician section 624 for some or all of the search options utilized in search component 608. For instance, the Dr. Quinn section 624 includes a checkbox for specialty, subspecialty, insurance match, location, and language. In the example depicted, all the check boxes are displayed as checked, indicating that the Dr. Quinn's attributes match the searched options. The physician's specialty may also be displayed, along with the physician's address and the health system to which the physician belongs. Other information relevant to the referral may also be provided, as necessary.

Within each physician section may be two actionable buttons: a referral button 626 and a view profile button 628. Upon selection of the referral button 626, a referral will be made to the physician within the respective physician section. For example, upon selection of the referral button 626, Dr. Quinn is referred (or an additional user interface is provided to facilitate such referral). Upon selection of the view profile button 628, additional information about the physician may be displayed. The additional information may be arranged and displayed, in embodiments, as a physician performance analysis 400 as depicted in FIGS. 4A-B. For example, upon selection of the view profile button 628, additional information about Dr. Quinn is displayed.

The physician sections for Dr. Gibbs 630 and Dr. Swanson 636 are substantially similar to the Dr. Quinn section 624. Each of the sections displays checkboxes for search options. For all three physicians in the results list, all the displayed check boxes are displayed as being checked. As such, each of the search criteria is matched. The order or rank of the physicians in the results list thus depends on additional factors, such as the recommendation determined in operation 510 in FIG. 5. For example, Dr. Quinn may have a more positive result metric than either Dr. Gibbs or Dr. Swanson. As such, Dr. Quinn is displayed higher in the results list than Dr. Gibbs or Dr. Swanson.

Figure 7:
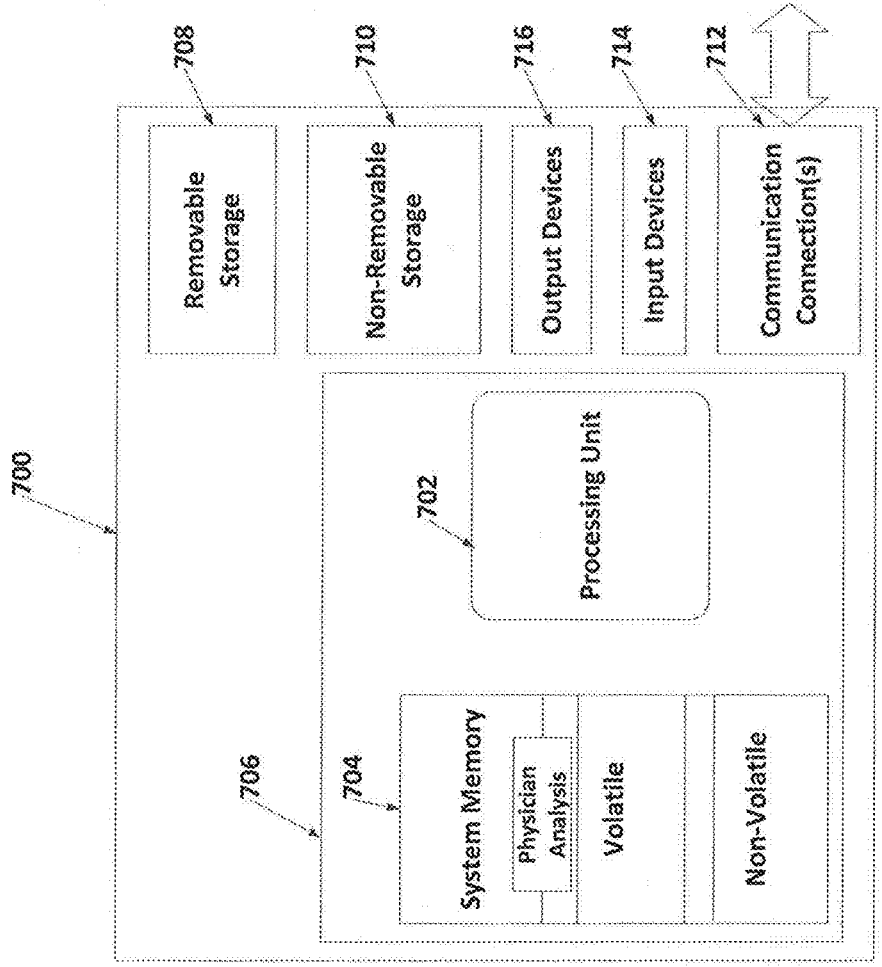
FIG. 7 illustrates one example of a suitable operating environment in which one or more of the present embodiments may be implemented.

FIG. 7 illustrates one example of a suitable operating environment 700 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smartphones, network PCs, minicomputers, mainframe computers, distributed computing environments that include any of the above systems or devices, and the like.

In its most basic configuration, the operating environment 700 typically includes at least one processing unit 702 and memory 704. Depending on the exact configuration and type of computing device, the memory 704 (storing, among other things, sequential chains constructed as described herein) may be volatile (such as RAM), non-volatile (such as ROM, flash memory, etc.), or some combination of the two. Memory 704 may store computer instructions related to generating a physician indicator, and/or displaying the various user interface embodiments disclosed herein. The memory 704 may also store computer-executable instructions that may be executed by the processing unit 702 to perform the methods disclosed herein.

This most basic configuration is illustrated in FIG. 7 by a dashed line 706. Further, the environment 700 may also include storage devices (removable, 708, and/or non-removable, 710) including, but not limited to, magnetic or optical disks or tape. Similarly, the environment 700 may also have input device(s) 714 such as a keyboard, mouse, pen, voice input, etc. and/or output device(s) 716 such as a display, speakers, printer, etc. Also included in the environment may be one or more communication connections, 712, such as LAN, WAN, point to point, etc.

The operating environment 700 typically includes at least some form of computer readable media. Computer readable media can be any available media that can be accessed by the processing unit 702 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible or non-transitory medium which can be used to store the desired information. Computer storage media does not include communication media.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media. In embodiments, the computer storage media may store physician indicators and information and instructions to create, modify, or otherwise interact with physician indicators and information.

The operating environment 700 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet.

Figure 8:
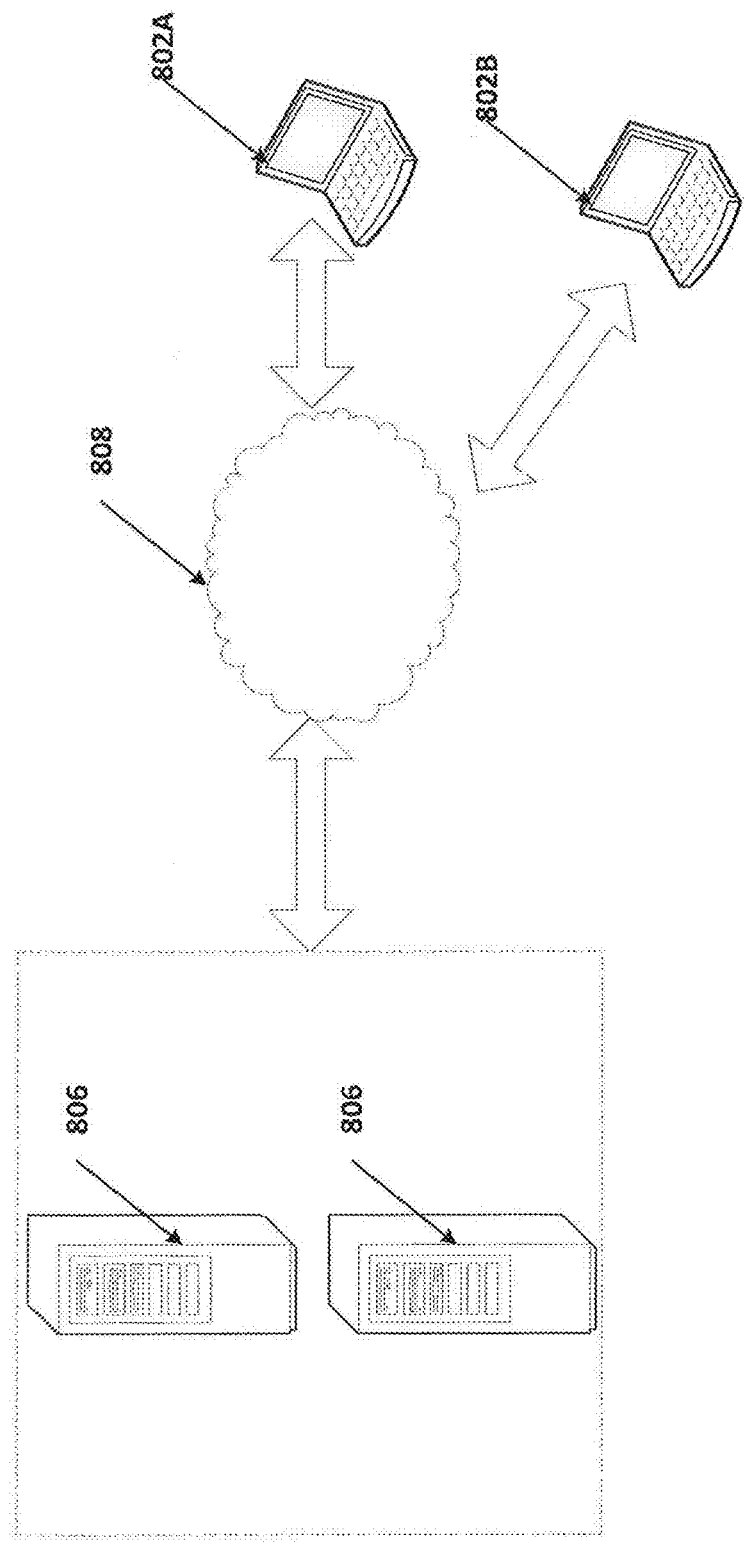
FIG. 8 depicts an embodiment of a network in which the various systems and methods disclosed herein may operate.

FIG. 8 is an embodiment of a network 800 in which the various systems and methods disclosed herein may operate. In embodiments, client devices, such as client devices 802A and 802B, may communicate with each other and one or more servers, such as servers 804 and 806, via a network 808. In embodiments, a client device may be a laptop, a personal computer, a smart phone, a PDA, a netbook, or any other type of computing device, such as the computing device in FIG. 8. In embodiments, the servers 804 and 806 may be any type of computing device, such as the computing device illustrated in FIG. 7. The network 808 may be any type of network capable of facilitating communications between the client devices 802A and 802B and one or more servers 804 and 806. Examples of such networks include, but are not limited to, LANs, WANs, cellular networks, and/or the Internet.

In embodiments, the various systems and methods disclosed herein may be performed by one or more server devices. For example, in one example, a single server, such as the server 804 may be employed to perform the systems and methods disclosed herein. The client device 802 may interact with the server 804 via network 808 in order to access information such as, information about physician indicators and information. In further embodiments, the client device 806 may also perform functionality disclosed herein, such as by displaying one of the disclosed forms and collecting information from a user.

In embodiments, the methods and systems disclosed herein may also be performed using a distributed computing network, or a cloud network. Data may be stored locally or remotely. One skilled in the term "receiving" is not intended to be limiting, and may include passive receipt and or active retrieval, such as pull or push type data transfer, or a combination thereof. In embodiments, the methods and systems disclosed herein may be performed by two or more servers, such as the servers 804 and 806. Although a particular network embodiment is disclosed herein, one of skill in the art will appreciate that the systems and methods disclosed herein may be performed using other types of networks and/or network configurations.

Although specific embodiments were described herein and specific examples were provided, the scope of the invention is not limited to those specific embodiments and examples. One skilled in the art will recognize other embodiments or improvements that are within the scope and spirit of the present invention. Additionally, the specific embodiments and examples described herein may be combined with one another. Therefore, the specific structure, acts, or media are disclosed only as illustrative embodiments. The scope of the invention is defined by the following claims and any equivalents therein.

What is claimed is:

1. A method for displaying physician analytics, the method comprising:
  receiving, at a processor, a value metric associated with a first physician;

receiving, at the processor, a value metric associated with a second physician;

receiving, at the processor, a quality metric associated with the first physician and a quality metric associated with the second physician, wherein the value metric and the quality metric are based on data from at least one of internal and external data sources, wherein an Application Program Interface (API) is used to share the data between the processor and the at least one of the internal and external data sources while the internal and external data sources house the data separately from a system comprising the processor;

based on the value metric and the quality metric for the first physician, and based on the value metric and the quality metric for the second physician, automatically generating, using the processor, a result metric for the first physician;

based on the value metric and the quality metric for the second physician, and based on the value metric and the quality metric for the first physician, automatically generating, using the processor, a result metric for the second physician, wherein the result metric for the first physician and the result metric for second physician are represented by at least one of a coordinate and a one-by-two matrix entry in a database, wherein two values in the one-by-two matrix entry are the value metric and the quality metric;

based on the result metric for the first physician, and relative to the result metric for the second physician, automatically generating an insight for the first physician;

based on the result metric for the second physician, and relative to the result metric for the first physician, automatically generating an insight for the second physician;

automatically generating, using the processor, a display for a user interface, comprising:
  a first axis representing the value metric;
  a second axis representing the quality metric;
  a first physician insight indicator, a visual characteristic of the first physician insight indicator representing the insight for the first physician, plotted with respect to the first and second axes, wherein a position of the first physician insight indicator represents the value metric for the first physician, the quality metric for the first physician, and the result metric for the first physician;
  a second physician insight indicator, a visual characteristic of the second physician insight indicator representing the insight for the second physician, plotted with respect to the first and second axes, wherein a position of the second physician insight indicator represents the value metric for the second physician, the quality metric for the second physician, and the result metric for the second physician; and
  a legend comprising a listing of at least one first physician insight and the at least one second physician insight; and outputting the user interface.

2. The method of claim 1, wherein displaying the first axis is one axis of a chart and the second axis is another axis of the chart.

3. The method of claim 1, further comprising receiving, at the processor, a quantity metric for the first physician, wherein the display further comprises a display of the quantity metric for the first physician.

4. The method of claim 3, wherein:
the display of the quantity metric for the first physician comprises a size of the first physician insight indicator plotted with respect to the first and second axes, wherein the size of the first physician insight indicator corresponds to a value of the quantity metric for the first physician.

5. The method of claim 3, wherein the quantity metric is based on at least one piece of data selected from the group consisting of: a number of patients of the first physician, a case volume for the first physician, a number of operations for the first physician, revenue share for the first physician, and the volume for the first physician, and the revenue for the first physician.

6. The method of claim 3, wherein the display further comprising displaying specific values for the value metric, the quality metric, and the quantity metric.

7. The method of claim 3, wherein the generated user interface is operable to receive user selections of at least one of the value metric, the quality metric, and the quantity metric.

8. The method of claim 1, wherein the insight for the first physician is based on one or more of: a type of training for the first physician, a hiring decision for the first physician, or a profile for the first physician.

9. The method of claim 8, wherein:
the visual characteristic of the first physician insight indicator is a color of the first physician insight indicator; and the legend correlates the color of the first physician insight indicator with a text description of the insight for the first physician.

10. The method of claim 9, wherein the visual characteristic of the first physician insight indicator insight is based on a location of the first physician insight indicator with respect to the first axis and the second axis.

11. The method of claim 9, wherein:
the first axis and the second axis are two axes of a chart; the chart comprises multiple segments; and
each segment corresponds to a different insight.

12. The method of claim 1, wherein the value metric indicates the first physician's value to a health system.

13. The method of claim 1, wherein the value metric is based on at least one or more of the group consisting of: contribution margin and revenue share.

14. The method of claim 1, wherein the quality metric indicates a quality of care provided by the first physician.

15. The method of claim 1, wherein the quality metric is based on at least one or more pieces of data from the group consisting of: 30-day readmission rate, mortality rate, and complications of care rate.

16. The method of claim 1, further comprising receiving, at the processor, a selection of the first physician insight indicator and, in response, generating a display comprising additional metrics for the first physician.

17. The method of claim 1, wherein the value metric is received from a first source and the quality metric is received from a second source.

18. A computer storage media comprising instructions that, when executed by one or more processors, cause at least one of the one or more processors to execute a method comprising:
receiving, at the processor, a value metric associated with a first physician;
receiving, at the processor, a value metric associated with a second physician;
receiving, at the processor, a quality metric associated with the first physician and a quality metric associated with the second physician, wherein the value metric and the quality metric are based on data from at least one of internal and external data sources, wherein an Application Program Interface (API) is used to share the data between the processor and the at least one of the internal and external data sources while the internal and external data sources house the data separately from a system comprising the processor;

based on the value metric and the quality metric for the first physician, and based on the value metric and the quality metric for the second physician, automatically generating, using the processor, a result metric for the first physician;

based on the value metric and the quality metric for the second physician, and based on the value metric and the quality metric for the first physician, automatically generating, using the processor, a result metric for the second physician, wherein the result metric for the first physician and the result metric for second physician are represented by at least one of a coordinate and a one-by-two matrix entry in a database, wherein two values in the one-by-two matrix entry are the value metric and the quality metric;

based on the result metric for the first physician, and relative to the result metric for the second physician, automatically generating an insight for the first physician;

based on the result metric for the second physician, and relative to the result metric for the first physician, automatically generating an insight for the second physician;

automatically generating, using the processor, a display for a user interface, comprising:
  a first axis representing the value metric;
  a second axis representing the quality metric;
  a first physician insight indicator, a visual characteristic of the first physician insight indicator representing the insight for the first physician, plotted with respect to the first and second axes, wherein a position of the first physician insight indicator represents the value metric for the first physician, the quality metric for the first physician, and the result metric for the first physician;
  a second physician insight indicator, a visual characteristic of the second physician insight indicator representing the insight for the second physician, plotted with respect to the first and second axes, wherein a position of the second physician insight indicator represents the value metric for the second physician, the quality metric for the second physician, and the result metric for the second physician; and
  a legend comprising a listing of at least one first physician insight and the at least one second physician insight; and
outputting the user interface.

19. A method for utilizing physician analytics, the method comprising:
receiving, at a processor, a value metric associated with a first physician;
receiving, at the processor, a value metric associated with a second physician;
receiving, at the processor, a quality metric associated with the first physician and a quality metric associated with the second physician, wherein the value metric and the quality metric are based on data from at least one of internal and external data sources, wherein an Application Program Interface (API) is used to share the data between the processor and the at least one of the internal and external data sources while the internal and external data sources house the data separately from a system comprising the processor;

based on the value metric and the quality metric for the first physician, and based on the value metric and the quality metric for the second physician, automatically generating, using the processor, a result metric for the first physician;

based on the value metric and the quality metric for the second physician, and based on the value metric and the quality metric for the first physician, automatically generating, using the processor, a result metric for the second physician, wherein the result metric for the first physician and the result metric for second physician are represented by at least one of a coordinate and a one-by-two matrix entry in a database, wherein two values in the one-by-two matrix entry are the value metric and the quality metric;

based on the result metric for the first physician, and relative to the result metric for the second physician, automatically generating an insight for the first physician;

based on the result metric for the second physician, and relative to the result metric for the first physician, automatically generating an insight for the second physician;

automatically generating, using the processor, a display for a user interface, comprising:
  a first axis representing the value metric;
  a second axis representing the quality metric;
  a first physician insight indicator, a visual characteristic of the first physician insight indicator representing the insight for the first physician, plotted with respect to the first and second axes, wherein a position of the first physician insight indicator represents the value metric for the first physician, the quality metric for the first physician, and the result metric for the first physician;
  a second physician insight indicator, a visual characteristic of the second physician insight indicator representing the insight for the second physician, plotted with respect to the first and second axes, wherein a position of the second physician insight indicator represents the value metric for the second physician, the quality metric for the second physician, and the result metric for the second physician; and
  a legend comprising a listing of at least one first physician insight and the at least one second physician insight;
outputting the user interface;
automatically generating, using the processor, a referral recommendation for the first physician based on the result metric for the first physician; and
automatically displaying, on the display, the referral recommendation.

20. The method of claim 19, wherein automatically generating the referral recommendation comprises adjusting, using the processor, a rank of the first physician in a search results list for a search for physician referrals.

* * * * *